United States Patent [19]

Kuroyanagi et al.

[11] Patent Number: 5,584,801
[45] Date of Patent: Dec. 17, 1996

[54] WOUND COVERING

[75] Inventors: Yoshimitsu Kuroyanagi, Zama; Nobuyuki Shioya, Yokohama; Masaru Tsunoda, Hachioji; Hiromu Sato, Kusatsu, all of Japan

[73] Assignees: Kotec Limited, Ogaki; Mitsubishi Kasei Corporation, Tokyo, both of Japan

[21] Appl. No.: 140,127
[22] PCT Filed: May 6, 1992
[86] PCT No.: PCT/JP92/00582
    § 371 Date: Mar. 10, 1994
    § 102(e) Date: Mar. 10, 1994
[87] PCT Pub. No.: WO92/19194
    PCT Pub. Date: Nov. 12, 1992

[30] Foreign Application Priority Data

May 7, 1991 [JP] Japan ................... 3-101427

[51] Int. Cl.⁶ ........................................... A61F 13/00
[52] U.S. Cl. .................. 602/47; 602/48; 602/52; 602/900; 424/447
[58] Field of Search .................... 602/42, 43, 47, 602/48, 52; 424/447; 604/265, 266

[56] References Cited

U.S. PATENT DOCUMENTS

| 3,888,247 | 6/1975 | Stenvall | 602/128 |
| 4,541,426 | 9/1985 | Webster | 128/156 |
| 4,542,012 | 9/1985 | Dell | 424/28 |
| 4,667,665 | 5/1987 | Blanco et al. | 128/156 |
| 4,990,144 | 2/1991 | Blott | 604/304 |
| 5,035,893 | 7/1991 | Shioya et al. | 424/447 |
| 5,061,258 | 10/1991 | Martz | 604/307 |

FOREIGN PATENT DOCUMENTS

| 0006714 | 1/1980 | European Pat. Off. . |
| 0059048 | 9/1982 | European Pat. Off. . |
| 0282771 | 9/1988 | European Pat. Off. . |
| 55-5699 | 1/1980 | Japan . |
| 59-57654 | 4/1984 | Japan . |
| 59-205959 | 11/1984 | Japan . |
| WO89/01345 | 2/1989 | WIPO . |
| WO90/10424 | 9/1990 | WIPO . |

Primary Examiner—Corrine M. McDermott
Assistant Examiner—Chalin Smith
Attorney, Agent, or Firm—Oblon, Spivak, McClelland, Maier & Neustadt, P.C.

[57] ABSTRACT

A wound covering comprising a film formed of a polyurethane resin, or a laminate of the polyurethane film and an absorptive cloth, wherein the polyurethane film or the cloth contains an antibacterial agent, and perforations are formed at least on the polyurethane film.

6 Claims, No Drawings

WOUND COVERING

TECHNICAL FIELD

The present invention relates to wound coverings. More particularly, it relates to wound coverings comprising a polyurethane resin film having an excellent water vapor permeability (hereinafter referred to simply as a polyurethane film), or laminate comprising such a polyurethane film and an absorptive cloth.

BACKGROUND TECHNIQUE

The properties mainly required for wound coverings are 1. adhesiveness, 2. flexibility, 3. durability, 4. ease in handling, 5. shelf stability, 6. blocking property against bacteria, 7. affinity to a vital body, 8. hemostatic property, 9. water-vaporization controlling ability, 10. exudate-draining property, etc.

In treating a wound such as a burn, although the treating method depends on the depth and area of the wound, it is common to use a wound covering comprising a polyurethane resin or a silicone resin, or an artificial skin (a wound covering) made of e.g. chitosan, collagen or a chitosan-collagen complex (Japanese Unexamined Patent Publication No. 253065/1986), or to apply a cream containing an antibacterial agent (Geben cream, trade name) to the burn, cover it with a gauze and fix the gauze by a bandage.

In the method in which a cream containing an antibacterial agent (Geben cream, trade name) is applied to the burn, and a gauze is put thereon and fixed by a bandage, it is necessary to change the gauze in a frequency of from several times per day to once in several days, and there are problems that cumbersome operations give a great deal of pain to a patient and require substantial care by the treating person.

Further, among wound coverings currently used, few have properties 1. to 10. described above, and they are still far from being satisfactory.

On the other hand, a cultured skin which uses cells derived from the skin and is aimed at a permanent take, is used in treatment of a burn patient, in addition to a wound covering which covers the wound surface temporarily. However, it is difficult for a cultured skin to maintain a constant take rate because of its weakness in physical strength and resistance against infection. In order to improve the take rate of a cultured skin, it is important to form a better transplantation bed. It is also desired to study such a covering which is capable of providing a suitable environment for the take of such a cultured skin.

DISCLOSURE OF THE INVENTION

The object of the present invention is to overcome (1) the drawbacks in the method wherein a cream containing an antibacterial agent (Geben cream, trade name) is applied to a burn, and a gauze is placed thereon and fixed with a bandage, and (2) the drawbacks of the currently used wound coverings. Namely, it is an object of the present invention to provide a wound covering, of which the side in contact with an affected part such as a burn is made of a film-like material with excellent adhesive properties to a vital body and excellent detachment ability from the wound surface, and if necessary, an absorptive cloth is provided on the other side to improve the water-vaporization controlling ability, and an antibacterial agent is incorporated in the film or the cloth to provide blocking properties against bacteria. It is also an object of the present invention to provide a wound covering which has a function that exudate, which has an adverse effect in treatment if it stays at the affected part, can be drained off easily. It is also an object of the present invention to provide a wound covering that is easy to handle.

Namely, the present invention provides a wound covering comprising a film of a polyurethane resin, or a laminate of the polyurethane film and an absorptive cloth, wherein an antibacterial agent is incorporated in the polyurethane film or the cloth, and perforations are formed at least on the polyurethane film.

BEST MODE FOR CARRYING OUT THE INVENTION

Now, the wound covering of the present invention will be described in detail.

The polyurethane resin to be used for the polyurethane film of the present invention may be any polyurethane resin, as long as it is excellent in adhesive properties, flexibility, water vapor permeability, and detachment ability from the wound surface. As examples of a preferable polyurethane resin, the following polyurethane resin may be mentioned.

A random copolymer of tetrahydrofuran (hereinafter referred to simply as THF) and ethylene oxide (hereinafter referred to simply as EO) is used as a polyol component. The copolymer is synthesized by ring opening copolymerization of a mixture of THF and EO in the presence of a Lewis acid catalyst such as boron trifluoride etherate complex by using water or a short chain diol such as ethylene glycol or 1,4-butane diol as an initiator.

The content of EO units in the random copolymer of THF and EO is preferably from 20 to 80% by weight, more preferably from 30 to 70% by weight, most preferably from 40 to 70% by weight. The random copolymer of THF and EO preferably has a number-average molecular weight of from 800 to 3,000. If the number-average molecular weight is smaller than 800, the polyurethane film will be hard. If the number-average molecular weight is larger than 3,000, the polyurethane film will be too adhesive and will increase swelling upon absorption of water. To obtain the best physical properties of the film, taking flexibility into consideration, the number-average molecular weight is preferably 1,000 to 2,500.

If necessary, a polyol such as polytetramethylene ether glycol (hereinafter referred to simply as PTMG), polyethylene glycol, polypropylene glycol, polybutylene adipate, polycaprolacton diol, polycarbonate diol or silicon polyol, may be incorporated to the random copolymer of THF and EO. PTMG is often used. In this case, PTMG having a number-average molecular weight of 800 to 3,000 is preferably used, and the number-average molecular weight of the polyol mixture is preferably 800 to 3,000. To obtain a polyurethane film having a better balance of physical properties, it is desirable that the polyol mixture has a number-average molecular weight of 1,000 to 2,500.

The above-mentioned random copolymer of THF and EO may partly contain a partial block copolymer structure formed at the time of polymerization, in the polyol chains, without departing from the spirit of the present invention.

As a copolymer of THF and EO, in addition to the above, a block copolymer can be obtained by adding EO to PTMG obtained by ring opening polymerization of THF, or by adding THF to polyethylene glycol (hereinafter referred to simply as PEG) obtained by ring opening polymerization of EO. However, the polyurethanes obtained by using these block copolymers have a highly hydrophilic EO homopolymer long chain in their structures. Therefore, swelling upon absorption of water tends to substantially increase with an increase of the EO content in the total amount of the polyurethane similar to the case where PTMG is used in the combination with PEG. Thus, there is a practical problem in their use.

The present invention has been accomplished on the basis of the finding that when the above random copolymer of THF and EO is used as a polyol component of the polyurethane, the resulting polyurethane surprisingly shows a high water vapor permeability, while the increase of water absorption due to the increase of EO units is less than that of a block copolymer of THF and EO, or a system in which PTMG and PEG are used in combination.

A polyurethane resin suitable for use in the present invention is obtained usually by a method wherein the above specified polyol is reacted with an excessive amount in equivalent of a diisocyanate at a temperature of 70° to 120° C. to form an urethane prepolymer having terminal isocyanate groups, and then the chain of the prepolymer is extended by a chain extender in an organic solvent at a temperature of 20° to 100° C. In this case, the ratio in equivalent of the diisocyanate to the polyol in the urethane prepolymer is usually from 1.5:1 to 6:1. It is preferred that the ratio is from 1.8:1 to 4.5:1, to obtain both good physical properties and water vapor permeability.

Examples of the diisocyanate in the polyurethane resin to be used in the present invention include aromatic diisocyanates such as 4,4'-diphenylmethane diisocyanate, 2,4- or 2,6-tolylene diisocyanate, 1,5-naphthalene diisocyanate and m- or p-phenylene diisocyanate, alicyclic diisocyanates such as isophorone diisocyanate, 4,4'-dicyclohexylmethane diisocyanate, 1,4-cyclohexylene diisocyanate and hydrogenated tolylene diisocyanate, and aliphatic diisocyanates such as hexamethylene diisocyanate.

Among them, alicyclic diisocyanates are preferred because the resulting polyurethanes will be free from yellowing and will have good mechanical properties. Although these are usually used alone, two or more of them may be used in combination. Among alicyclic diisocyanates, 4,4'-dicyclohexylmethane diisocyanate is most preferred in view of the balance of mechanical properties and water vapor permeability of the resulting film.

Examples of the chain extender for the polyurethane resin to be used in the present invention include low molecular weight diols such as ethylene glycol, propylene glycol, diethylene glycol, 1,4-butanediol and 1,6-hexanediol, aliphatic diamines such as ethylenediamine, 1,2-propanediamine, tetramethylenediamine and hexamethylenediamine, alicyclic diamines such as isophoronediamine, 4,4'-dicyclohexylmethanediamine, 3,3'-dimethyl-4,4'-dicyclohexylmethanediamine and 1,4-cyclohexylenediamine, hydrazine hydrate, and water. Among them, alicyclic diamines are preferred since the resulting film will have a good thermal resistance. They may be used alone or in combination as a mixture of at least two of them. A low molecular weight diol described above may be used with them, within a range in which mechanical properties and thermal resistance of the resulting film will not be deteriorated. Among the aliphatic diamines, isophorone diamine is particularly preferred, in view of the stability of the solution and the balance of film properties.

As an organic solvent used in the synthesis of the polyurethane resin to be used in the present invention, a solvent with strong solvency such as dimethylformamide, dimethylacetamide and dimethyl sulfoxide, is suitable. They may be used alone or as a mixture with at least one member selected from the group consisting of solvents of aromatic type such as toluene and xylene, solvents of ketone type such as methyl ethyl ketone, acetone and cyclohexanone, solvents of acetate type such as ethyl acetate and butyl acetate, chlorine-containing solvents such as dichloroethane, solvents of ether type such as tetrahydrofuran and dioxane, and solvents of alcohol type such as methanol and isopropanol.

It is preferred that the resulting polyurethane resin contains 15 to 60% by weight of ethylene oxide units. If the content of ethylene oxide units is less than 15% by weight, the water vapor permeability of the film will be insufficient. If it is more than 60% by weight, the dimensional change due to swelling at the time of water absorption and the deterioration of physical properties will be substantial, such being undesirable.

In the present invention, if necessary, a catalyst which is usually used to accelerate a urethane-forming reaction, e.g. a tertiary amine such as triethylenediamine, or an organotin compound such as dibutyltin dilaurate, may be present at the time of the synthesis of the polyurethane.

To improve the durability of the polyurethane resin of the present invention, one or more of an antioxidant of hindered phenol type, an ultraviolet light absorber of benzophenone type or benzotriazole type and a stabilizer of hindered amine type may be incorporated. In this case, each additive is added in an amount of from 0.05 to 3% by weight of the solid content of the polyurethane. To obtain a good effect with a small amount of the additive, the amount of the additive is preferably from 0.2 to 1% by weight. In the polyurethane of the present invention, a stabilizer of hindered amine type is particularly effective and can reduce the oxidative deterioration at the time of sterilization treatment and the deterioration of physical properties by hydrolysis.

In the present invention, the ethylene oxide units mentioned above represent the proportion by weight percentage of ethylene oxide to tetrahydrofuran and ethylene oxide.

With respect to a method of film-formation, it is known that by making a polyurethane film porous, high water vapor permeability can be obtained. Examples of such a method include (1) a wet film-formation method wherein a polyurethane resin solution is coated on a support, and the solvent and other soluble substances are extracted in a coagulating bath, and (2) a method wherein a W/O emulsion of polyurethane resin is coated on a support and then heated and dried to obtain a porous film.

To obtain a porous film from a polyurethane resin solution, a dry film-formation method may be employed wherein a solution is coated on a support or a release paper, and then heated to dry it, whereby a film having a constant water vapor permeability can be produced with a good reproducibility, and practically adequate strength, elongation and durability can be obtained even with an unsupported film.

The support used in the dry film-formation method is not particularly restricted. A polyethylene or polypropylene film, and release paper or cloth coated with a release agent of fluorine-type or silicone-type, may be employed.

Since the water vapor permeability of the polyurethane resin film used in the present invention has an inverse relation to the thickness of the film, it is preferred to use a release paper with a uniform thickness. The coating method is not particularly restricted, and a knife coater, a roll coater and any other coater may be used. Drying temperature is determined optionally depending upon the ability of the drier, but it is necessary to select a range of temperature to avoid insufficient drying and sudden removal of the solvent. The drying temperature is preferably within a range of from 60° to 130° C.

The thickness of the polyurethane resin film used in the present invention is usually from 10 to 200 μm, preferably from 10 to 50 μm. If the thickness is less than 10 μm, pinholes are likely to be formed at the time of coating and the film tends to undergo blocking whereby it will be difficult to handle the film. If the thickness is more than 50 μm, it is likely to be difficult to obtain adequate water vapor permeability. Besides, the film of the present invention is characterized in that the film thickness dependence of water vapor permeability is small as compared with that of other urethane films. A foaming agent may be incorporated to the polyurethane resin to form a foamed film. The expansion rate is usually from about 1.2 to 5 times.

The polyurethane resin film to be used in the present invention has a high water vapor permeability of at least 2,000 g/m$^2$·24 hr, preferably at least 3,000 g/m$^2$·24 hour (as measured according to JIS Z0208), when the film thickness is from 10 to 80 μm. If the water vapor permeability is less than this value, the film makes the skin stuffy and gives an unpleasant feeling when it is put on the skin, such being undesirable. The film has a 100% modulus of at least 20 kg/cm$^2$, preferably at least 30 kg/cm$^2$. If the 100% modulus is less than 20k g/cm$^2$, the film will be too adhesive, whereby it is likely to cause blocking between films. If it is more than 80 kg/cm$^2$, the film tends to have a poor flexibility and a low water vapor permeability.

In the present invention, although the above polyurethane film can be used as a wound covering by itself, it is used also in the form of a laminate of the polyurethane film and an absorptive cloth.

As the cloth to be used in the present invention, any cloth such as a knitted fabric or a nonwoven fabric may be used, so long as it is soft and has a structure which makes it absorptive. Regarding the adhesiveness to a wound surface, it is preferred to use a stretchable knitted or nonwoven fabric. A nonwoven fabric is usually produced by spraying fine fibers on a smooth plate surface and then entwining, welding or bonding them mutually. Depending upon the method of producing a nonwoven fiber, it is possible that the resulting woven fiber is easily stretchable in one direction and is hardly stretchable in another direction.

It is preferred that the knitted or nonwoven fabric to be used in the present invention has a relatively large stretchability.

The stretchability represents the proportion of the length of elongation to the original length by percentage at the time when a nonwoven fabric of 60 cm long and 6 cm wide is under a load of 1,500 g. With respect to a nonwoven fabric, the stretchability is desired to be from 30 to 200%, preferably from 40 to 150%.

Considering the flexibility, durability, workability and water-absorptivity, the desired thickness of the knitted or nonwoven fabric is about from 0.5 to 3 mm, preferably about from 0.5 to 2 mm.

With respect to the material of the knitted or nonwoven fabric, considering flexibility, durability, water-absorptivity, ability to support a water-absorptive resin, natural fibers such as wood pulp and cotton, regenerated fibers such as rayon and cuprammonium rayon, semisynthetic fibers such as acetate and synthetic fibers such as nylon, polyester and acryl are suitable. In particular, when a fiber blend comprising polyester fibers and rayon fibers in a weight ratio of about 6:4 to 8:2 is used to produce a nonwoven fabric, the heat generated during the manufacturing process provides a good stretchability to the resulting nonwoven fabric. In this case, with respect to the thickness of the fibers constituting the nonwoven fabric, the thickness of the polyester fibers is preferably from 0.5 to 3.0 d (denier) and that of the rayon fibers is preferably from 1.0 to 3.5 d. It is desired to make a difference in fineness between the polyester fibers and the rayon fibers so that the rayon fibers are thicker by about 0.5 d.

In the present invention, a cloth having a water-absorptive resin supported thereon may be used. As the water-absorptive resin to be used, a resin having hydrophilic groups (e.g. —OH, —COOH, —SO$_3$H and —NHCO—) is suitable. For example, water-absorptive resins of starch type, cellulosic water-absorptive resins and water-absorptive resins of synthetic polymer type, such as polyacrylic acid type, POVAL type and polyoxyethylene type, are suitable. Specifically, alginate, carboxyalkylcellulose and gelatin may, for example, be mentioned.

The water-absorptive resin is used as supported on the cloth. With respect to the supporting method, a method in which the cloth is made wet by e.g. spraying water on its surface and a water-absorptive resin is sprayed on it in a form of powder or fine particles, is preferred, because of the simplicity of the process. Powder of a water-absorptive resin absorbs water on the cloth surface and adheres to the fibers of the cloth, whereby it is supported. It is possible to use an adhesive component in addition to the water-absorptive resin, and it is used depending upon the particular use or purpose. The water-absorptive resin is used in an amount of from about 0.2 to 5 g, preferably from about 0.5 to 3 g, per 100 cm$^2$.

With respect to a method for laminating the polyurethane film and the cloth, a simple method is such that a polyurethane resin solution is coated and heat-dried on a support or a release paper, and before it is completely dried during the dry film-forming, the nonwoven fabric is put thereon, followed by pressing. Further, there is a method wherein after producing a polyurethane film, a solvent is sprayed on the film surface to swell the film, and then a cloth is put thereon and pressed, or a method wherein after producing a polyurethane film, a cloth is bonded to the film with an adhesive. When the cloth is bonded with an adhesive, the adhesive is applied in a dotted pattern or to fiber portions of the cloth, because, if the adhesive is applied to the entire surface of the film, the water vapor permeability of the film will be impaired. The polyurethane film may be provided on one side of the cloth. However, to control the vaporization property, such films may be provided on both sides of the cloth.

As the antibacterial agent to be used in the present invention, an antibacterial agent effective to genus Pseudomonas, Enterobacter, Klebsiella, Staphylococcus or *E. coli* is preferred. For example, antibacterial agents of sulfonamide type, cephalosporin type, penicillin type, nalidixic acid type, macrolide type, polypeptide type and aminoglycoside type may be used.

Such an antibacterial agent is impregnated into the polyurethane film, or, in the case of the laminate, impregnated in the polyurethane film or the cloth. With respect to the method for impregnating the antibacterial agent, it is possible to impregnate it into polyurethane raw material or into the raw material of the cloth, to impregnate it into the cloth, or to spray a polymer solution containing an antibacterial agent onto the cloth so that the antibacterial agent is supported on the cloth in the form of microbeads. The amount of the antibacterial agent depends on the type of the agent and the particular purpose, and can not generally be defined. It is determined appropriately as the case requires.

Then, perforations are formed on the polyurethane film or the laminate thus obtained. The perforations may be formed by a method wherein a roller having a lot of cutter blades is permitted to roll on the film surface of the laminate to form perforations. In the case where the polyurethane films are provided on both sides of a nonwoven fabric, perforations may be provided on the wound surface side only, or on both sides.

The shape of the perforations may be in the form of pinholes, punched holes, cross-shaped slits or straight slits. Considering the water-absorptivity and water retention characteristic, the straight slit form is particularly preferred. It is preferred that the longitudinal direction of the slits is intersectional to the easily stretchable direction of the cloth. By forming the slits as described above, the slits can change their opening areas in correspondence with the stretching degree of the cloth. The length of the slits is preferably about 2 to 5 mm, and the slits may be arranged in any pattern such as in a parallel or zigzag pattern.

The role of the perforations is to facilitate drainage (removal) of exudate which is likely to exude in a large quantity at the initial stage when the wound covering is applied. Namely, fluid accumulation is avoided by small perforations mechanically formed on the composite. Soon after application of the wound covering, exudation decreases, and the exudate solidifies to close the perforations. This surprising treatment effect has never been generally known. Therefore, the composite sheet or the polyurethane film itself is required to have a high water vapor permeability.

The wound covering of the present invention is used so that the polyurethane film side is in contact with the wound part. It may take any optional shape such as a bandage-like shape or a patch-like shape of from a few to a few tens centimeters square. It is selected depending upon the degree and size of the wound. In case of a patch-shaped wound covering, it is required to be fixed by a tape or a bandage. Accordingly, a bandage-like shape is preferred for simplicity in handling.

Now, the present invention will be described in further detail with reference to Examples. However, it should be understood that the present invention is by no means restricted to such specific Examples.

PREPARATION EXAMPLES 1 TO 3

Preparation of THF-EO Random Copolymers

THF and EO were randomly copolymerized in an autoclave at a temperature of 30° C. under atmospheric pressure, by using ethylene glycol as an initiator and boron trifluoride ethyl etherate as an acid catalyst, in the following proportions: 17.2 parts by weight of ethylene glycol, 241.4 parts by weight of THF, 241.4 parts by weight of EO and 19.7 parts by weight of boron trifluoride ethyl etherate. After the polymerization, the acid catalyst in the product was neutralized by alkali, and the precipitate was collected by filtration and then dehydrated at 100° C. by blowing dried nitrogen thereto.

The resulting THF-EO random copolymer (hereinafter referred to as polyol) is a colorless transparent liquid and has a number-average molecular weight of 1,800 and an EO content of 50% by weight (polyol A).

A polyol was prepared in the same manner as in Preparation Example 1, except for changing the proportions as follows: 28.2 parts by weight of ethylene glycol, 236 parts by weight of THF, 236 parts by weight of EO and 32.3 parts by weight of boron trifluoride ethyl etherate. The resulting polyol was a colorless transparent liquid and had a number-average molecular weight of 1,100, and an EO content of 50% by weight (polyol B).

A polyol was prepared in the same manner as in Preparation Example 1, except for changing the proportions as follows: 13.4 parts by weight of ethylene glycol, 194.6 parts by weight of THF, 291.9 parts by weight of EO and 15.3 parts by weight of boron trifluoride ethyl etherate. The resulting polyol was a colorless transparent liquid and had a number-average molecular weight of 2,300 and an EO content of 60% by weight (polyol C).

The number-average molecular weight was calculated by measuring the hydroxyl number. The EO content was calculated from the amounts of charged raw materials.

PREPARATION EXAMPLES 4 TO 6

Preparation of Polyurethane Resins (a) Preparation of polyurethane solutions 359.6 parts by weight of polyol A obtained in Preparation Example 1, 104.7 parts by weight of 4,4'-dicyclohexylmethane diisocyanate (diisocyanate component A) and 35.7 parts by weight of isophorone diamine were reacted in a flask under dry nitrogen at 100° C. for 6 hours, to form a urethane polymer having terminal isocyanate groups. Then, a chain extending reaction of the urethane polymer was conducted in a dimethylformamide solvent by using isophorone diamine as a chain extender while maintaining the temperature at 30° C., to obtain a colorless, transparent viscous solution having a polyurethane solid content of 25% by weight. The polyurethane solution had a viscosity of 20,000 cps at a temperature of 25° C., and an EO content of 36% by weight (Preparation Example 4).

A polyurethane solution was prepared in the same manner as in Preparation Example 5 except that 305.7 parts by weight of polyol B, 145.6 parts by weight of diisocyanate component A and 48.7 parts by weight of isophorone diamine were used. The polyurethane solution had a viscosity of 35,000 cps at a temperature of 25° C., and an EO content of 31% by weight (Preparation Example 5).

A polyurethane solution was prepared in the same manner as in Preparation Example 5 except that 383.0 parts by weight of polyol C, 87.3 parts by weight of diisocyanate component A and 29.7 parts by weight of isophorone diamine were used. The polyurethane solution had a viscosity of 15,000 cps at a temperature of 25° C. and an EO content of 46% by weight (Preparation Example 6).

(b) Preparation of a polyurethane film

The above polyurethane solutions were diluted with methanol so that their concentrations would be 1% by weight. To the resulting methanol solutions, antibacterial agents such as sulfadiazine silver, gentamicin and polymyxin B were admixed at a concentration within a range of from 0.01% by weight to 0.1% by weight (to the polyurethane solution of Preparation Example 4, sulfadiazine was admixed at a concentration of 0.1% by weight (A); to the polyurethane solution of Preparation Example 5, gentamicin was admixed at a concentration of 0.01% by weight (B); to the polyurethane solution of Preparation Example 6, polymyxin B was admixed at a concentration of 0.01% by weight (C)). Each of these mixed solutions was poured onto a glass plate, spread by using a glass bar to coat it in a uniform thickness, and dried overnight at 80° C. to obtain three kinds of colorless transparent polyurethane dry films (films A, B and C). At the time of coating, the film thickness was adjusted to about 25 μm by using a spacer.

The water vapor permeability was determined in accordance with JIS Z-0208 by measuring the weight by means of a water vapor permeability cup under a condition of 40° C. and 90% RH.

Film A: water vapor permeability 4,400 g/m$^2$-24 hr
Film B: water vapor permeability 3,500 g/m$^2$-24 hr
Film C: water vapor permeability 4,800 g/m$^2$-24 hr

PREPARATION EXAMPLES 7 TO 9

Bonding of the Polyurethane Film and Nonwoven Fabric

As the nonwoven fabric, a nonwoven fabric having a thickness of 0.8 mm and 100 g/m$^2$, which comprised rayon fibers with an average fineness of 3 d and polyester fibers of 2.5 d in a weight ratio of 22:78, was used. The nonwoven fabric had stretchabilities of 47% in a longitudinal direction and 128% in a transverse direction. The nonwoven fabric was permitted to absorb a small amount of a 50/50 solution of methanol and water. Then, powder of sodium alginate as water absorptive resin was sprayed thereto at a rate of 0.7 g/100 cm$^2$. This fabric and a nonwoven fabric having no absorptive resin supported thereon were bonded to three types of polyurethane films of 25 μm thickness obtained in step (b) of Preparation Examples 4 to 6, followed by drying to obtain composites. Slit-like perforations of 3 mm length were provided on the polyurethane film of each sheet on straight lines at intervals of 2 mm in a direction perpendicular to the transverse direction of the film, with the pitch of said lines (parallel distance between the lines) being 5 mm, so that slits will be arranged in a zigzag pattern.

Among the composites wherein film A was used, the one having the absorptive resin supported thereon is designated as Preparation Example 7(*a*), and the one having no absorptive resin is designated as 7(*b*). Among the composites wherein film B was used, the one having the absorptive resin supported thereon is designated as Preparation Example 8(*a*), and the one having no absorptive resin is designated as Preparation Example 8(*b*). Among the composites wherein film C was used, the one having the absorptive resin supported thereon is designated as Preparation Example 9(*a*), and the one having no absorptive resin is designated as Preparation Example 9(*b*).

EXAMPLE 1

The bonded porous composites obtained in the above Preparation Examples 7(*a*), 8(*a*) and 9(*a*) were sterilized by ethylene oxide gas and then subjected to the following test. All films and sheets used in Examples hereinafter were subjected to the test after sterilizing treatment.

Dorsal full-thickness skin defect (30×40 mm) was created in each rat (SP rats of 6 to 8 weeks old) (12 cases) surgically, and the obtained composites were put thereon followed by suturing their circumferences. Gauzes were put on them followed by bandaging with elastic bands. 4 cases for each of the three types of films, i.e. a total of 12 cases were used. After one or two weeks, adhesiveness to the vital body, reconstruction of false dermis were observed histologically on 2 cases per each of three types of films, to confirm their effectiveness. Even after two weeks, sodium alginate powder remained as swelled upon absorption of water, thus showing the function of preventing the wound surface from dryness. It was found that all the sheets have a good healing effect and are suitable as wound coverings.

EXAMPLE 2

The three types of bonded composites obtained in the above Preparation Examples 7(*b*), 8(*b*) and 9(*b*) were sterilized by ethylene oxide gas and then subjected to the following test.

The covering effects of the three types of bonded composites were examined on dorsal full-thickness skin defect of rats.

Full-thickness skin defect of a size of 3 cm×3 cm was surgically formed on dorsa of 5 week-old rats (12 cases), and the obtained composites were put thereon followed by bandaging with elastic bands. 10 cases were used for each types of film, i.e. 30 cases were used in total. After 1, 2, 3, 4, and 5 weeks, 2 rats were killed under anesthesia at a time to observe drainage of the covered surface, adhesiveness and contracture of the wound surface. In addition, tissues on the wound surface were sectioned and fixed by 10% formalin, and then preparations were made and subjected to hematoxylin-eosin (HE) staining, to evaluate histologically the conditions of the wound surfaces.

Slit-shaped trace of exude was observed on each gauze on the wound covering. Fluid accumulation was not observed, whereby it was shown that drainage went favorably. Since the wound covering adhered to the wound surface slightly, no mechanical damage was given to the wound surface. There was no trace of intrusion of neoblast into the fiber of the nonwoven fabric through the slits. It is considered that coagulation of exude which intruded through the slits gave the slight adhesiveness. Even after 5 weeks, there was no contracture of the wound surface observed. This is considered to be attributable to the existence of the nonwoven fabric supported behind the polyurethane film.

In the observation of tissues on the wound surface after 1 or 2 weeks, granulation tissues with a lot of neutrophiles and giant cells caused by foreign bodies were observed. However, in the observation of tissue after 3 to 5 weeks from the application of the covering, the appearance of neutrophiles and giant cells caused by foreign bodies terminated and a good false dermis formation was observed.

EXAMPLE 3

The preventing effect of *Ps. aeruginosa* (type strain GN11189) proliferation inoculated on agar media was examined by using the composites obtained in the above Preparation Example 7(*b*).

*Ps. aeruginosa* was inoculated on agar media of 90 mm diameter at a density of 1×10$^5$/cm$^2$, and the wound covering of the present invention (4 cm×4 cm) was put thereon, followed by cultivation at 37° C. for two days. Then, the agar under the covering was cut into pieces of 1 cm$^2$ size, and the pieces were put into 10 ml of sterilized physiological saline and stirred at 15,000 rpm to obtain a mother liquor. The mother liquor was diluted 10 times and 0.1 ml of the diluted liquid was inoculated on an agar culture medium prepared afresh, followed by cultivation at 37° C. for one day. After the cultivation, the number of formed colonies was counted to determine the number of *Ps. aeruginosa* present under the wound covering. Designating this operation as Stage I, the same operation was repeated. At the time of repeating, the wound covering used in Stage I was put on an agar culture medium on which *Ps. aeruginosa* was newly inoculated to examine the antibacterial activity. This operation is designated as Stage II. Further, the wound covering used in Stage II was used in the operation of Stage III.

*Ps. aeruginosa* was inoculated on an agar culture medium at a density of $1 \times 10^5/cm^2$ and the number of bacteria detected after 2 days from the inoculation was used as a control group. The results are shown below. In the control group, *Ps. aeruginosa* at a density % 8.9 to $9.4 \times 10^8/cm^3$ were detected. However, when the wound covering of the present invention was present, there was no *Ps. aeruqinosa* detected in any of Stage I to III. By this, it was shown that the wound covering of the present invention has a persistent effect for preventing bacterial proliferation.

| | Number of *Ps. aeruginosa* ($\times 10^8/cm^2$) | | |
|---|---|---|---|
| | Stage I | Stage II | Stage III |
| Control | 8.9 | 9.1 | 9.4 |
| Under wound covering | 0 | 0 | 0 |

Mean value in 5 measurements for each stage

EXAMPLE 4

A cytotoxicity of the antibacterial agent released from the wound covering of the present invention was measured by using the laminate obtained in the above Preparation Example 7(b).

(a) Cytotoxicity test by using cultured epidermis

A small skin graft left in a dermatoplasty was peeled off into epidermis and dermis by dispase treatment, and from the resulting epidermis, epidermal cells were collected by tripsin treatment. The epidermal cells were cultivated for 2 weeks in the presence of a feeder layer of 3T3 cells in accordance with Green's method (Proc. Natl. Acad. Sci. USA, 76, 5665–5668, 1979), and then subjected to dispase treatment to prepare cultured epidermis. A stainless net of 3 mm height was placed in a culture plate of 90 mm diameter, and a sponge sheet of collagen was put thereon. Further, cultured epidermis (4 cm×4 cm) was put on it, followed by addition of 25 ml of culture medium so that the cultured epidermis would be situated at the interface of the medium and air (since when cultured epidermis is situated at a medium-air interface, keratinization is accelerated, it is considered as reasonable to evaluate cytotoxicity by putting the wound covering under such a condition). The wound covering of the present invention was put on the cultured epidermis under such a condition and allowed to stand in an incubator at 37° C. for 4 days. After the incubation, the wound covering was taken off and the cultured epidermis was partly cut together with the sponge sheet of collagen and fixed by 10% formalin to make a preparation. After staining the preparation by trypan blue, the number of surviving cells was counted using a hemacytometer.

The one prepared without putting the wound covering of the present invention on the cultured epidermis was used as a control. For comparison, with respect to the one prepared by putting a gauze (4 cm×4 cm) evenly coated with Geben cream (manufactured by Tokyo Tanabe Co., Ltd.), which contained a sulfadiazine silver similar to the sulfadiazine silver impregnated in the wound covering of the present invention, on the cultured epidermis, the number of surviving cells was counted.

The results are shown below. The number of surviving cells in the cultured epidermis to which the wound covering of the present invention was applied was about 50% of that in the control group to which no covering was applied and kept in the order of $10^5$, whereas no epidermis cell survived under the gauze coated with Geben cream. From this, it was proved that the wound covering of the present invention had no remarkable cytotoxicity and little side effect.

| Number of surviving epidermal cells ($\times 10^5/cm^2$) | |
|---|---|
| Control group | 3.16 |
| Under the wound covering | 1.63 |
| Geben cream | 0 |
| Under the gauze coated | |

Mean value in 2 measurements for each experiment (b) Cytotoxicity test by using a composite cultured dermis Since fibroblasts can not aggregate in a form of a sheet by itself, as being different from epidermal cells, it is necessary to incorporate some matrix to form a three-dimensional aggregate which is used as a model of dermis. Accordingly, a composite cultured dermis in which collagen was used as a matrix was prepared.

Dermis peeled off by the above-mentioned method was treated with a solution mixture of 0.1% collagenase and 0.2% hyaluronidase to obtain fibroblasts and the fibroblasts were subcultured using a Delbecco's modified Eagle's Medium containing 10% fetal bovine serum as a medium. According to the method of Kuroyanagi et al., *Journal of Japan Plastic Surgery*, 11, 515–531, 1991, the subcultured fibroblasts were inoculated on a collagen matrix at a density of $5 \times 10^5$ cells/$cm^2$ and cultivated for a week to prepare a composite cultured dermis. A stainless net of 3 mm height was placed in a culture plate of 90 mm diameter, a composite cultured dermis (4 cm×4 cm) was put on it upside down, and 25 ml of medium was added so that the composite cultured dermis would be situated at the interface of the medium and air. (When the composite cultured dermis is situated at a medium-air interface upside down, a collagen gel layer incorporating fibroblast in three dimensions is allowed to be immersed in the medium, whereby the cells will not be damaged. Therefore, it is possible to evaluate the effect of the antibacterial agent released from the wound covering placed at the medium-air interface on the cells). Under such a condition, the wound covering of the present invention was put on the composite cultured dermis and then it was allowed to stand in an incubator at 37° for 1 to 3 days. After the incubation, the composite cultured dermis was cut into a size of 3 cm×3 cm and allowed to stand in 5 ml of 0.5% collagenase solution at 37° C. for 30 minutes followed by stirring, to obtain a cell suspension. After staining by trypan blue, the number of the surviving cells was counted using a hemacytometer. For comparison, with respect to the one prepared by putting a gauze (4 cm×4 cm) evenly coated with Geben cream (manufactured by Tokyo Tanabe Co., Ltd.) which contained sulfadiazine silver similar to the sulfadiazine silver contained in the wound covering of the present invention on the composite cultured dermis, the number of surviving cells was counted similar. In a preliminary test, it was confirmed that when only the composite cultured dermis was put on the stainless net similar to the above-mentioned manner, there was no change in the cell number.

The results are shown below. After 3 days, compared with before the test, the number of surviving fibroblasts was 42% and kept in the order of $10^5$, whereas, under the gauze coated with Geben cream, the number of surviving cells was zero. Therefore, it was proved that the wound covering of the present invention has no remarkable cytotoxicity against fibroblasts and little side effect.

|  | Number of surviving epidermal cells ($\times 10^5/cm^2$) | Cellular viability (%) |
| --- | --- | --- |
| Before test | 5.5 | — |
| After 1 day | 4.0 | 73 |
| After 2 days | 4.6 | 84 |
| After 3 days | 2.3 | 42 |
| Gauze coated with Geben cream | 0 | 0 |

Mean value in 2 measurements for each experiment

EXAMPLE 5

Using the composite obtained in the above Preparation Example 7(b), a preliminary clinical testing of the wound covering of the present invention was made.

The wound coverings of the present invention (hereinafter referred to simply as UF) cut into 12×20 cm were applied to patients with decubitus, burn, dermatomic wound (wound at donor site of a split-thickness skin graft) skin defect, abrasion and epidermal abrasion (see Table 1), as cut in accordance with the case of the wounds.

After cleaning and disinfecting the wound surfaces, the UFs were directly applied thereto and covered with sterilized dry gauzes followed by fixing the gauzes with tapes while applying slight pressure. The UFs were used without replacing for from 2 to 14 days depending upon the case of wound or the degree of contamination. When epithelialization of the wound surface or a good granulation bed was not observed at the time of the replacement, the UF was newly applied.

For the purpose of comparative experiment, lyophilized porcine dermis was used in properly selected cases. In the comparative experiment, the lyophilized porcine dermis was applied adjacent to the wound covering of the present invention followed by similar treatment (half side test).

After application of UFs, the gauzes and the wound coverings were changed and observed properly and the degree of pain, adhesiveness, degree of fusion or breakage of the wound covering, exudate-draining properties, detachment ability of the wound covering, conditions of the wound surface, healing period, infection preventing effect, frequency of change of bandage and existence of side effect were synthetically evaluated. The results are given below. From these results, it is proved that the wound covering of the present invention can be applied in treatments of various wound surfaces.

Results (1) Burn

II degree superficial burn (SDB)

In all of 8 cases, by changing only gauzes 1 to 3 times and no wound covering, the wound surfaces were epithelialized without infection. Although in some cases, epithelialization seemed to have completed several days before removal of the wound covering, the burns were healed in 6 to 11 days and the UFs could be detached without pain. UF is considered to be effective in healing SDB.

II degree deep burn (DDB)

Good granulation tissues were formed without infection. There was no pain during the application. The possibility of temporary use to epidermization was indicated.

III degree deep burn (DB)

The burn was covered with dry eschar for about a week and did not adhere to the UF. However, the eschar part fused with the elapse of time. In the case of a serious wound, in the initial stage of burn, when a lot of exudate exuded, since no fluid accumulation was observed under the UF, UF was kept as it was and only the covering gauze was changed. Frequent bandaging is difficult in a broad burn. In this respect, UF is very effective in avoiding troublesome bandaging.

(2) Wounds at donor site of a split-thickness skin graft

As thick-split dermatomic wound has a homogeneous wound surface, a lyophilized porcine dermis was applied at the same time to examine the effectiveness of UF in comparison. As a result, no difference was observed in the epithelialization.

(3) Decubitus

UF was applied on 8 cases classified as to be II–V degree by Compbell (*Surg. Clin. North. Am.*, 37, 509–530, 1959). The interval to exchange bandage was 2–6 days with good management and good granulation tissues were formed under controlling infection.

(4) Skin defect

UF was considered to be effective in the formation of good granulation tissues, in temporary covering before self skin graft and in acceleration of epithelialization.

(5) Abrasion and epidermal abrasion

No pain was observed during the application period but that disinfection treatment at the time when UF were replaced. No UF shift from the original area was observed during the application period. After epithelialization, UF could be detached easily without incurring any pain.

TABLE 1

| Indication cases | No. | Age | Sex | Location | Indication wounds | Area (cm) | Operation | Days used | Interval dressing | Patch frequency | Previous history |
| --- | --- | --- | --- | --- | --- | --- | --- | --- | --- | --- | --- |
| Burn | 1 | 8 | Male | Trunk, lower leg | SDB | 15% | — | 8 days | 8 days | 1 | |
| | 2 | 3 | Male | Bilateral buttock | SDB,* | 1.5% | — | 7 days | 2–5 days | 1 | |
| | 3 | 2 | Female | Left thigh | SDB | 1% | — | 8 days | 2–4 days | 1 | |
| | 4 | 7 | Female | Chest | SDB | 1% | — | 11 days | 4–7 days | 1 | |
| | 5 | 10 | Male | buttock | SDB | 2% | — | 9 days | 4–5 days | 1 | |
| | 6 | 5 | Female | Left lower leg | SDB | 1% | — | 9 days | 4–5 days | 1 | |
| | 7 | 47 | Female | Left lower leg | SDB | 3% | — | 11 days | 4–7 days | 1 | |
| | 8 | 50 | Male | Lower jaw, neck | SDB | 4% | — | 6 days | 6 days | 1 | |
| | 9 | 10 | Male | Bilateral lower leg | SDB | 11% | — | 8 days | 1 days | 1 | |
| | 10 | 50 | Male | Right waist | SDB, DDB | 0.5% | — | 21 days | 4–7 days | 5 | |

TABLE 1-continued

List of UF use cases

| Indication cases | No. | Age | Sex | Location | Indication wounds | Area (cm) | Operation | Days used | Interval dressing | Patch frequency | Previous history |
|---|---|---|---|---|---|---|---|---|---|---|---|
| | 11 | 5 | Male | Left thigh | SDB, DDB | 4% | Operation | 41 days | 3–7 days | 10 | |
| | 12 | 3 | Male | Left shoulder, arm | SDB, DDB | 3% | — | Still in use | 4–6 days | — | |
| | 13 | 22 | Female | Left forearm | DB | 0.5% | Operation | 7 days | 7 days | 1 | |
| | 14 | 20 | Female | Right thigh (back) | SDB, DDB, DB | 4% | Operation | 21 days | 7 days | 4 | |
| | 15 | 52 | Male | Trunk left arm | SDB, DDB, DB | 37% | Operation | 16 days | 3–8 days | 8 | |
| Doner site of split-thickness skin graft | 16 | 60 | Male | Right buttock | * | 4 × 7 | | 11 days | 11 days | 1 | |
| | 17 | 5 | Male | Right buttock | * | 5 × 7 | | 14 days | 14 days | 1 | |
| | 18 | 42 | Male | Right buttock | * | 10 × 18 | | 14 days | 14 days | 1 | |
| | 19 | 42 | Male | Left buttock | | 10 × 18 | | 11 days | 11 days | 1 | |
| | 20 | 62 | Female | Left thigh | | 10 × 15 | | 14 days | 14 days | 1 | RA |
| | 21 | 52 | Male | Right buttock | * | 10 × 18, 8 × 18 | | 14 days | 14 days | 1 | |
| | 22 | 52 | Male | Left buttock | * | 10 × 18, 8 × 18 | | 14 days | 14 days | 1 | |
| | 23 | 52 | Male | Right thigh (front) | * | 10 × 20 | | 9 days | 9 days | 1 | |
| | 24 | 52 | Male | Left thigh (front) | * | 10 × 20 | | 9 days | 9 days | 1 | |
| | 25 | 52 | Male | Right thigh (back) | * | 10 × 18 | | 10 days | 10 days | 1 | |
| | 26 | 52 | Male | Left thigh (back) | * | 8 × 18, 7 × 16 | | 10 days | 10 days | 1 | |
| | 27 | 52 | Male | Lower abdomen | * | 10 × 20 | | 10 days | 10 days | 1 | |
| | 28 | 77 | Female | Left buttock | * | 10 × 15 | | 12 days | 12 days | 1 | |
| Decubitus | 29 | 78 | Male | Sacrum | 5 | 4 × 2.5 | — | 95 days | 3–5 days | 29 | Diabetes |
| | 30 | 61 | Male | Sacrum | 5 | φ 4 | — | 78 days | 3–4 days | 22 | Pnemonia |
| | 31 | 83 | Male | Sacrum | 5 | φ 5 | — | Still in use | 3–4 days | 1 | Cerbral hemorrhage |
| | 32 | 82 | Female | Sacrum | 5 | 5 × 5 | — | 12 days | 4–6 days | 1 | Cerbral infarction |
| | 33 | 60 | Male | Sacrum | 5 | 16 × 13 | Operation | 14 days | 1–2 days | 13 | Intraspinal contriction |
| | 34 | 60 | Male | Greater trochanter | 4 | 2.5 × 3 | Operation | 14 days | 2–3 days | 6 | Intraspinal contriction |
| | 35 | 69 | Male | Greater trochanter | 3 | φ 2.5 | — | 16 days | 3–4 days | 5 | Intraspinal contrication |
| | 36 | 77 | Male | Right heel | 2 | φ 3 | — | 10 days | 4–6 days | 2 | Cerbral hemorrhage |
| Skin defect | 37 | 81 | Female | Left 2nd finger | | φ 1 | Operation | 25 days | 3–7 days | 6 | ASO |
| | 38 | 24 | Male | Right foot | | 6 × 5 | Operation | 10 days | 3–4 days | 3 | — |
| | 39 | 22 | Male | Left 2nd finger | | φ 0.7 | — | 14 days | 3–7 days | 3 | — |
| | 40 | 68 | Male | Left 4th finger | | φ 0.9 | — | 19 days | 3–7 days | 5 | — |
| | 41 | 69 | Male | Right sole | | φ 3 | — | 65 days | 3–7 days | 16 | Diabetes |
| | 42 | 69 | Male | Left sole | | φ 3.5 | — | 76 days | 3–7 days | 18 | Diabetes |
| | 43 | 52 | Male | Left arm | After debleedman | 6% | — | 8 days | 8 days | 1 | DB |
| Abrasion | 44 | 21 | Male | Face | Post-operative | 1.5 × 5 | | 8 days | 8 days | | |
| | 45 | 18 | Female | Right neck | Post-operative | 2.5 × 3 | | 9 days | 4–5 days | 1 | |
| | 46 | 61 | Female | Face | | φ 3 | | 5 days | 5 days | 1 | |
| | 47 | 21 | Male | Left lower leg | | φ 5 | | 14 days | 3–4 days | 3 | |
| | 48 | 4 | Female | Left foot | | φ 3 | | 12 days | 3–4 days | 2 | |
| | 49 | 26 | Male | Left forearm | | φ 2 | | 5 days | 5 days | 1 | |
| Epidermal abrasion | 50 | 60 | Male | Left waist | | φ 2.5 | | 4 days | 4 days | 1 | |
| | 51 | 42 | Male | Left neck | | 1 × 2 | | 4 days | 4 days | 1 | |

*Half side test: porcine sknin was used in all cases.

PREPARATION EXAMPLE 10

The polyurethane solution obtained in Preparation Example 5 was diluted with a solution mixture comprising dimethylformamide, methyl ethyl ketone and isopropanol to a concentration of 10% by weight, and Gentamicin as an antibacterial agent was incorporated to the resulting solution at a concentration of 1 mg per ml of the solution.

Using this solution mixture, a film of 30 mm thickness was prepared in the same manner as in the above Preparation Examples 4 to 6(b), and slits of 5 mm in length were formed at intervals of 5 mm.

EXAMPLE 6

The covering effect of the polyurethane film obtained in the above Preparation Example 10 was examined. The healing process (especially, the drainage of exudate and the adhesiveness to a cultured skin) was observed as follows:

Experimental Method

Example 6(a)

After 4 pieces of cultured artificial skin (6.5 cm×9.0 cm) derived from heteroplasm were grafted to a part of human right thigh (donor site, 0.015 inch), the wound covering of the present invention was applied thereto and covered with and fixed by a sterilized gauze.

Example 6(b)

A cultured artificial skin was grafted to a wound at donor site of a split-thickness skin graft (0.020 to 0.025 inch) on human right brachium and antebrachium, and the wound covering of the present invention was applied thereto and covered with and fixed by a sterilized gauze.

Results

Example 6(a)

On the 9th day after the experiment started, no fluid accumulation was observed beneath the wound covering of the present invention, and the adhesiveness between the cultured skin and the wound covering of the present invention was good. The wound covering could be released without pain, and epithelialization proceeded favorably.

Example 6(b)

No fluid accumulation was observed beneath the wound covering of the present invention, and the adhesiveness to the cultured skin was good. The wound covering of the present invention was replaced at an interval of 10 to 15 days, and when detached, it could be easily detached simply by soaking it in saline. Reconstitution of skin was observed 3 weeks after grafting.

From the results as described above, it is apparent that the wound covering of the present invention is effective as a wound covering to be applied on cultured skin.

INDUSTRIAL APPLICABILITY

The wound covering of the present invention is excellent in adhesiveness, flexibility, durability, ease of handling, shelf stability, blocking property against bacteria, affinity to a vital body, water-vaporization controlling ability and exudate-draining property, and is very effective to patients with skin ulcer, decubitus, burns, or wounds at the donor site of a split-thickness skin graft. It is also effective as a covering capable of providing a suitable environment for the take of a cultured skin.

We claim:

1. A method for covering a wound, comprising:

applying to the wound a laminate film consisting essentially of a polyurethane film and an absorptive cloth, in such manner that said polyurethane film is in direct contact with the wound;

wherein said polyurethane film comprises a polyurethane resin which is the product of a diisocyanate with a random copolymer of tetrahydrofuran and ethylene oxide;

wherein said random copolymer contains from 20 to 80% by weight of ethylene oxide units and has a number-average molecular weight of from 800 to 3,000;

wherein said polyurethane resin is extended by a chain extender; and said polyurethane film having an antibacterial agent incorporated in said polyurethane film, and wherein said polyurethane film has at least one slit-form perforation formed therein.

2. The method of claim 1, wherein said antibacterial agent is sulfadiazine silver, gentamicin or polymyxin B.

3. The method of claim 1, wherein said laminate film is capable of been applied to a wound selected from the group consisting of burn, thick-split dermatomic wound, ducubitus, skin defect, abrasion and epidermal abrasion.

4. The method of claim 1, wherein said absorptive cloth is a non-woven fabric.

5. The method of claim 4, wherein said non-woven fabric has a stretchability of 80% under a load of 250 g/cm in at least one direction and wherein said slit-form perforation is formed in a direction intersectional to the easily stretchable direction of the non-woven fabric.

6. The method of claim 4, wherein said non-woven fabric is made of a fiber blend of a polyester fibers and a rayon fiber.

* * * * *